US005506208A

United States Patent [19]
Eyal et al.

[11] Patent Number: 5,506,208
[45] Date of Patent: Apr. 9, 1996

[54] METHOD FOR USING SYNTHETIC ANALOGS OF THROMBOSPONDIN FOR INHIBITING ANGIOGENESIS ACTIVITY

[75] Inventors: Jacob Eyal, Baltimore; Bruce K. Hamilton, Silver Spring, both of Md.; George P. Tuszynski, Williamstown, N.J.

[73] Assignees: W. R. Grace & Co.-Conn., New York, N.Y.; The Medical College of Pennsylvania, Philadelphia, Pa.

[21] Appl. No.: 408,181

[22] Filed: Mar. 22, 1995

Related U.S. Application Data

[63] Continuation of Ser. No. 131,565, Oct. 4, 1993, abandoned, which is a continuation of Ser. No. 895,764, Jun. 9, 1992, abandoned, which is a division of Ser. No. 587,197, Sep. 24, 1990, Pat. No. 5,190,920.

[51] Int. Cl.⁶ .............. A61K 38/00; C07K 7/00; C07K 7/06; C07K 5/12
[52] U.S. Cl. .............. 514/17; 514/16; 530/327; 530/329
[58] Field of Search .............. 514/16–17; 530/329

[56] References Cited

U.S. PATENT DOCUMENTS

| 5,190,918 | 3/1993 | Deutch et al. | 514/15 |
| 5,192,744 | 3/1993 | Bouck et al. | |
| 5,200,397 | 4/1993 | Deutch et al. | 514/15 |

OTHER PUBLICATIONS

Tuszynski, et al, J. Biol Chem, 262, pp. 9718–9723, 1987.
Henessy, et al. J. of Cell Biol. 168, pp. 729–736 1989.
Tuszynski, et al. Cancer Research, 47, 4130–33, 1987.
Riser, et al, Experimental Cell Research 174 pp. 319–329, 1988.

*Primary Examiner*—Jill Warden
*Assistant Examiner*—S. G. Marshall
*Attorney, Agent, or Firm*—Burns, Doane, Swecker and Mathis

[57] ABSTRACT

Methods of use of compounds and compositions comprising fragments and synthetic analogs of human thrombospondin are provided for promoting or inhibiting thrombospondin-like activity.

10 Claims, 11 Drawing Sheets

METHOD FOR USING SYNTHETIC ANALOGS OF THROMBOSPONDIN FOR INHIBITING ANGIOGENESIS ACTIVITY

This application is a continuation of application Ser. No. 08/131,565, filed Oct. 4, 1993, now abandoned, in turn, a file wrapper continuation of prior application Ser. No. 07/895,764, filed Jun. 9, 1992, and now abandoned, which is a division of application Ser. No. 07/587,197, filed Sep. 24, 1990 now U.S. Pat. No. 5,190,920.

TECHNICAL FIELD

The present invention relates generally to peptide fragments and synthetic analogs of thrombospondin (TSP) which retain thrombospondin-like activity. The peptides retain and mimic the bioactivity of TSP as a potent promoter or inhibitor of cell adhesion and attachment to different cell lines. The peptides find use as agents in inhibiting metastasis since TSP has previously been shown to mediate tumor cell metastasis presumably by mechanisms involving the cell adhesive domain of TSP. These peptides also find use in different biological and pharmaceutical applications such as: (a) promoting and inhibiting cellular attachment to tissue culture flasks, (b) promoting wound healing, angiogenesis, and implant acceptance, (c) use as agents for antiplatelet aggregation and (d) use as diagnostic reagents in different therapeutic applications.

BACKGROUND

Thrombospondin (also known as thrombin sensitive protein or TSP) is a 450,000 molecular weight protein composed of three identical disulfide-linked polypeptide chains (Lawler et al. *J. Cell Biol* (1986) 101:1059–71). TSP is secreted by platelets in response to physiological activators such as thrombin and collagen (Lawler, *J. Blood* (1986) 67:112–123). TSP comprises 3% of the total platelet protein and 25% of the total platelet alpha granular protein (Tuszynski, G. P. et al. (1985) *J. Biol. Chem.* 260:12240–12245). Other cells also synthesize TSP including fibroblasts (Jaffe, E. A. et al., (1983) *Natl. Acad. Sci. USA* 80:999–1002), smooth muscle cells (Raugi, G. J. et al., (1982) *J. Cell Biol.* 95:351–354), and endothelial cells (McPhearson, J. et al. *J. Biol. Chem.* 256:11330–11336). TSP has been found in certain tumor tissues, such as melanoma cells (Varani, J. et al., (1989) *Clin. Expl. Metastasis* 7:319–329), squamous lung carcinoma (Riser, B. L. et al., (1988) *Exp. Cell Res.* 174:319–329) and breast carcinoma (Pratt, D. A. et al., (1989) *Eur. J. Cancer Clin. Oncol.* 25:343–350). In addition, the following tumor cells in culture have been shown to synthesize TSP: fibrosarcoma, rhabdomyosarcoma, glioblastoma, Wilm's tumor, neuroblastoma, teratocarcinoma, choriocarcinoma, melanoma, and lung carcinoma (Mosher, D. F., (1990) *Annu. Rev. Med.* 41:85–97). A number of recent studies have shown that TSP plays a major role in cell-cell and cell substratum adhesion (Tuszynski, G. P. et al., (1987) *Seminars in Thrombosis Hemostasis* (13:361–368, Mosher, D. F., (1990) *Annu. Rev. Med.* 41:85–97). TSP promotes cell attachment, platelet aggregation, and lung tumor colony formation in a murine model of experimental metastasis (Tuszynski, G. P. et al., (1987) *Science* 236:1570–1573, Tuszynski, G. P. et al., (1988) *Blood* 72:109–115). The role of TSP in adhesion is further supported by the observation that the extracellular matrix of most tissues contains TSP.

TSP is composed of linear polypeptide domains that specifically interact with various macromolecules such as plasma and matrix components. For example, TSP forms a complex with heparin (Yabkowitz, R. et al. (1989) *J. Biol. Chem.* 264:10888–10896), fibrinogen (Tuszysnki, G. P. et al. (1985) *J. Biol. Chem.* 260:12240–12245), collagen (Mumby, S. M. et al. (1984) *J. Cell Biol.* 98:10888–10896, and plasminogen (Depoli. P. et al. (1989) *Blood* 73:976–902). The structure of TSP is conserved among various animal species as indicated by the fact that the antibody against the human protein cross-reacts with TSP from mouse, rat, pig, cow, sheep, dog, and turkey (Switalska, H. I. et al., *J. Lab Clin. Med.* 106:690–700).

Thrombospondin has been purified by a number of procedures including exclusion chromatography (Lawler et al., *J. Biol. Chem.* (1978) 253:8609–16), heparin affinity chromatography (Lawler et al., *Thromb. Res.* (1981) 22:267–269), fibrinogen affinity chromatography (Tuszynski et al., *J. Biol. Chem.* (1985) 260:12240–5), barium chloride precipitation (Alexander et al., *Biochem. J.* (1984) 217:67–71) and anion exchange chromatography with HPLC (Clezarolin et al., *J. Chromatog.* (1984) 296:249–56).

The complete amino acid sequence of TSP has been deduced from DNA clones prepared by various groups including Lawler et al., *J. Cell Biol.* (1986) 103:1635–48; Kobayashi et al., *Biochemistry* (1986) 25:8418–25; Dixit et al., *Proc. Ntl. Acad. Sci.* (1986) 83:5449–53; and Hennessy et al., *J. Cell Biol.* (1989) 108:729–36.

Cell adhesion is critical to the development and survival of multicellular organisms. The process of cell adhesion is complex requiring numerous extracellular proteins such as fibronectin, vitronectin, collagen, laminin, and TSP and numerous families of cellular receptors such as the integrins and cellular adhesion molecules (CAMS). These molecules are involved in the adhesion of both normal and tumor cells and have been studied quite intensively in recent years.

The amino acid sequence, Arg-Gly-Asp (RGD), was established as a cell attachment domain in fibronectin (Pierschbacher, M. D. and Ruoslahti, E., (1984) *Nature* (London) 309:30–32). The same or related sequences have been discovered in many proteins and serve as cell binding sites for such macromolecules as fibrinogen (Ginsberg, M. D. et al., (1985) *J. Biol. Chem.* 260:11891–11896). However, it appears that the adhesive function of laminin may not be based on the RGD sequence, but on a peptide segment of the B1 chain containing the amino acid sequence tyrosine-isoleucine-glycine-serine-arginine (YIGSR) (Sasaki, M. 1987, *Proc. Natl. Acad. Sci* 84:935–938). Synthetic peptides containing the RGD and YIGSR sequence promote cell adhesion.

The therapeutic use of synthetic peptides based on the adhesive domains of fibronectin and laminin have recently been reported. Humphries et al. (2986) *Science* 233:467–470) were the first to demonstrate that co-injection of the pentapeptide GRGDS with B16-F10 murine melanoma cells dramatically inhibited the formation of lung colonies in C57BL/6 mice. Another synthetic peptide which was derived from laminin (YIGSR) also dramatically inhibited B16-F10 melanoma cell metastasis in C57B1/6 mice (Kleinman, H. K. et al., (1987) *Science* 238:1132–1133; Kleinman, H. K. et al., (1990) *Proc. Natl. Acad. Sci. USA* 87:2279–2283). The inhibitory activity of these peptides may be due to competition with endogenous laminin and fibronectin-dependent adhesion of tumor cells to the vascular bed of the target organ during the metastatic dissemination of the tumor cells.

Because metastasis is a step-by-step process involving the transfer of tumor cells from one site to another through the lymphatic and blood circulation and platelet reduction in animals effectively blocked metastasis in animals (Gasic et al, (1968) *Proc. Natl. Acad Sci USA* 48:46–52), platelets have been thought to play a special role in the development of metastasis. Since TSP comprises 25% of the total alpha granular platelet secreted-protein, TSP would be expected to have a major role in the hemotagenous transfer of tumor cells to distant organs. Indeed, TSP has been shown to promote tumor cell metastasis in a murine model (Tuszynski et al, (1987) 47:4130–4133). In addition, events which accompany platelet activation, such as: secretion of adhesive proteins, platelet aggregation, activation of proteolytic enzymes, and activation of the clotting cascade have all been shown to play a significant role in tumor cell metastasis (Gasic, G. J., (1984) *Cancer Metastasis Rev.* 3:99–116).

Adhesive proteins which are part of the extracellular matrix control the movement, growth, and morphology of many cell types. Extracellular matrix proteins interact with tumor cell receptors and affect tumor cell adhesion to basement membrane collagen in different ways. For example, exposure of melanoma cells in vitro to laminin resulted in increased capacity of tumor cells to adhere to the basement membrane and to produce lung tumor colonies (Barsky, S. H. et al., (1984) *J. Clin. Inv.* 74:843–848; Terranova, V. P. et al., (1984) *Science* 226:982–985).

In view of the information described above, TSP may play an important role in many diverse and clinically important processes, such as: cell migration, wound healing, nerve regeneration, and tumor cell metastasis. To better understand the pathophysiology of these processes at the molecular level, assignment of each of the biological activities of TSP to a specific subdomain or oligopeptide of TSP would provide valuable information. Specifically, detailed knowledge of the structure of domains of the TSP and TSP receptors could be used to design TSP antagonist peptides which could block pathophysiological activities of TSP such as TSP-dependent tumor cell metastasis formation.

TSP contains three homologous peptide sequences designated type I, II, and III repeats (Lawler and Hynes, (1986) *J. Cell Biol.* 103:1635–1648). The three repeats consist of approximately 60 amino acids each containing six cysteine residues. Type I repeats exhibit homology with peptide segments found in a number of diverse proteins. We have identified two hexapeptide sequences in TSP (CSTSCG and CSVTCG) that are either totally conserved in other proteins or present with one or two conservative amino acid substitutions. The prevalence of the conserved sequences is indicated in Table I below.

TABLE I

| Protein | Sequence | Reference |
|---|---|---|
| TSP | CSVTCG | Lawler et al., (1986), |
|  | CSTSCG | J. Cell Biol. 103:1635–48 |
| Circumsporozoite | CSVTCG | Dame J. B. et al., (1984) |
|  |  | Science 225:593–599 |
| Trap | CSVTCG | Robson K. J. H. et al., (1988) |
|  |  | Nature 335:79–82 |
| Properdin | CSVTCG | Goundis, D. et al. (1988) |
|  |  | Nature 335:82–85 |
| Glycoprotein E Herpes simplex I | CVVTCG | McGoech D. J. et al, (1985) J. Mol. Biol. 181:1–13 |
| Cytochrome C oxidase polypeptide II | CSETCG | Lawson, J. E. et al., (1985) Curr. Genet. 9:351–360 |
| Respiratory nitrate reductase beta chain | CSVTCK | Blasco, F. et al. (1989) Mol. Gen. Genet. 218:249–256 |
| Bird spider 18S ribosomal RNA | CSVSCG | Hendriks L. et al., (1989) Eur. J. Biochem. 177:15–20 |

TABLE I-continued

| Protein | Sequence | Reference |
|---|---|---|
| Chicken alpha tubulin | CSVVCG | Lemischka I. R. et al. (1981) J. Mol. Biol. 151:101–120 |
| Zebrafish homeobox gene | CSKTCG | Njolstad P. R. et al., (1990) EMBO J. 9:515–524 |
| E. coli gut operon | CSVTCX | Yamada M. et al., (1987) Biol. Chem. 262:5455–5463 |
| E. Coli ATPase | CSVTCM | Kanazawa H. et al., (1981) BBRC:103:613–620 |
| Rat liver apolipoprotein A-I | CSVGCG | Poncin J. E. et al., (1984) Eur. J. Biochem. 140:493 |
| Tryptophan synthetase | CWVTCG | Brosius, J. et al., (1982) Gene 17:223–228 |
| Highlands J virus | CSVTCL | Ou J. H. et al., (1982) J. Mol. Biol. 156:719–730 |
| Human c-myb proto-oncogene | CSVTCK | Slamon D. J. et al., (1986) Science 233:347–351 |
| Antistasin | CRKTCP | Ginsberg V. et al. (1990) |
|  | CRVHCP | J. Biol. Chem. 264:12138–12140 |
| Etp100 | CVCECG | Tomley F. et al (1989) |
|  | CSATCT | 5th International Cocciosisis |
|  | CSRTCG | Conference 469–573 |
|  | CSEQCG |  |
| Human desmin | CSVTCH | Li Z. et al., (1989) Gene 78:243–254 |
| Human related mammary tumor virus | CSVPCG | May F. E. B. et al., J. Virol 60:743–749 |
| Human proto-oncogene c-fes/fps | CSRTCG | Ouweland A. M. W. et al., EMBO J. 4:2897–2903 |
| Platelet GPIIb | CSVTCR | Bray P. F. et al., (1987) J. Clin. Invest. 80:1812–1817 |

The present invention provides thrombospondin fragments and analogs which mimic or inhibit the biological activity of intact thrombospondin which find use in a variety of biological, prophylactic or therapeutic areas.

SUMMARY OF THE INVENTION

It has now been found that a class of fragments or synthetic analogs from a specific domain of thrombospondin have a variety of uses. These peptides, by means of their adhesive activity, are capable of modifying and inhibiting tumor cell metastasis, cell adhesion and platelet aggregation in mammals in vivo. The peptides are also useful in wound healing, as diagnostic reagents and in other related areas. The peptides are capable of promoting cellular attachment and therefore can be used for preparing surfaces for optimal cell culture, derivatization of various prosthetic materials, and to promote binding of surrounding tissues. Medical devices can also be designed which make use of such substrates to attract cells to a surface in vivo or even to promote the growing of a desired cell type on a particular surface prior to grafting. The TSP peptides and analogs of this invention have been shown to have thrombospondin-like activity.

The present invention is, therefore, in one aspect directed to polypeptide compounds having thrombospondin-like activity which are identified by the formula:

$$R_1\text{-Cys-}X_2\text{-}X_3\text{-}X_4\text{-Cys-}R_2$$

wherein:

$R_1$ is a protected or unprotected terminal amino group, including hydrogen, amino, acetyl or at least one amino acid residue or the desamino form thereof;

$X_2$, $X_3$, and $X_4$ are the same or different neutral/non-polar/large/non-cyclic or neutral/polar/large/non-cyclic or neutral/polar/small or basic/non-cyclic amino acid residues, preferably selected from the group consisting of valine, threonine, serine, and arginine;

$R_2$ is a protected or unprotected terminal carboxyl group including hydroxyl, carboxyl, or at least one amino acid residue, including carboxyamide or alkylamide forms thereof, preferably selected from the group consisting of lysine, glycine, and arginine;

the structure of the polypeptide is optionally cyclized through a bond between the cysteines, preferably a disulfide bond, or a bond between $R_1$ and $R_2$.

Also provided in accordance with aspects of the invention are pharmaceutical compositions which contain the above-recited polypeptide compounds together with a pharmaceutically acceptable liquid, gel or solid carrier. Administration of therapeutically effective doses of these compositions can provide effective enhancement or inhibition of thrombospondin-like activity to animals, particularly vertebrates such as mammalian and avian hosts.

DETAILED DESCRIPTION OF THE INVENTION

Figure 1:
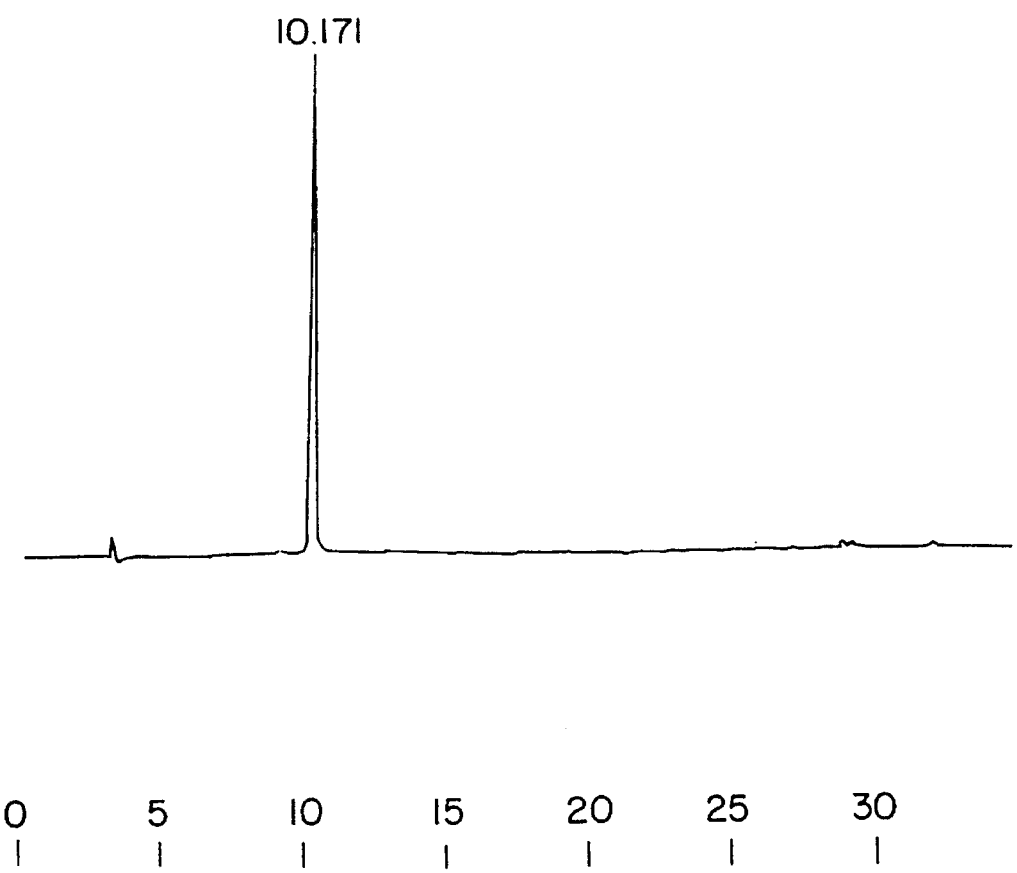
FIG. 1 shows the results of HPLC analysis on peptide CSVTCG-NH$_2$.

In accordance with the present invention, a class of fragments and analogs of thrombospondin is provided which is capable of inhibiting or mimicing the activity of thrombospondin in mammals in vivo.

A. Definitions

"Thrombospondin-like activity" is defined herein as any activity that mimics the known biological activities of thrombospondin. These activities include cell-adhesion promoting activity, cell mitogenic activity, cell chemotactic activities, and hemostatic activities and any activities that derive from these activities such as tumor cell, microbial, or parasite metastasis activity, platelet aggregating activity, fibrinolytic activity and immune modulation.

"Antimetastatic activity" is defined herein as the ability to prevent or greatly reduce the extent or size of tumor cell metastasis, or inhibit or cause regression of primary solid tumors.

"Wound healing activity" is defined herein as the ability to increase the rate at which wounds heal or to improve the results of the healing process (i.e., less scarring, good response to tactile stimulus, etc.)

"Angiogenesis activity" is defined herein as the ability to inhibit or enhance the formation of blood vessels or lymph vessels.

"Growth factor activity" is defined herein as the ability to inhibit or promote cell proliferation.

"Cell adhesion activity" is defined herein as the ability to promote or inhibit the attachment of cells, preferably mammalian cells, to a substrate.

The sequence of amino acid residues of the present polypeptide compounds, the core pentapeptide, and preferred embodiments thereof, are defined in terms of amino acids of certain characteristics of particular subclasses.

Amino acid residues can be generally subclassified into four major subclasses as follows:

Acidic, i.e., the residue has a negative charge due to loss of H ion at physiological pH and the residue is attracted by aqueous solution so as to seek the surface positions in the conformation of a peptide in which it is contained when the peptide is in aqueous medium.

Basic, i.e., the residue has a positive charge due to association with H ion at physiological pH and the residue is attracted by aqueous solution so as to seek the surface positions in the conformation of a peptide in which it is contained when the peptide is in aqueous medium.

Neutral/non-polar, i.e., the residues are not charged at physiological pH and the residue is repelled by aqueous solution so as to seek the inner positions in the conformation of a peptide in which it is contained when the peptide is in aqueous medium.

Neutral/polar, i.e., the residues are not charged at physiological pH and the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not. To fit the definition of charged, a significant percentage (at least approximately 25% of the individual molecules are charged at physiological pH.

Amino acid residues can be further subclassified as cyclic or non-cyclic, a self-explanatory classification with respect to the side chain substituent groups of the residues, and as small or large. The residue is considered small if it contains a total of three carbon atoms or less. Small residues are, of course, always non-cyclic.

For the naturally occurring protein amino acids, subclassification according to the foregoing scheme is as follows:

Acidic: Aspartic acid and Glutamic acid;

Basic/non-cyclic: Arginine and Lysine;

Basic/cyclic: Histidine;

Neutral/polar/small: Glycine, Serine and Cysteine;

Neutral/polar/large/non-cyclic: Threonine, Asparagine and Glutamine;

Neutral/polar/large/cyclic: Tyrosine;

Neutral/non-polar/small: Alanine;

Neutral/non-polar/large/non-cyclic: Valine, Isoleucine, Leucine and Methionine;

Neutral/non-polar/large/cyclic: Phenylalanine and Tryptophan.

The protein amino acid proline, although within the classification neutral/non-polar/large/cyclic, is not included as an alternative due to its known effects on the secondary conformation of peptide chains.

Certain commonly encountered non-natural amino acids, such as desamino L.C. yrosine (des Tyr), agmatine (Agm), n-formyl tryptophan (f-Trp), alpha-aminoisobutyric acid (Aib), and sarcosine (Sar), statine, ornithine (Orn), homolysine, homoserine, homoarginine, norleucine (Nle), norvaline may also be incorporated into the compounds of the invention. Desamino tyrosine is incorporated at the N-terminus. Agmatine and statine are incorporated at the C-terminus. Based on the above definition, n-formyl Trp is neutral/non-polar/large/cyclic, Sar is neutral/non-polar/small, Aib is neutral/non-polar/non-cyclic, Orn is basic/non-cyclic, homolysine is basic/non-cyclic, homoserine is neutral/polar/small, homoarginine is basic/non-cyclic, norleucine is neutral/non-polar/large/non-cyclic, and norvaline is neutral/non-polar/large/non-cyclic.

The nomenclature used to describe polypeptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified. In the amino acid structure formulae, each residue is generally represented by a one-letter or three-letter designation, corresponding to the trivial name of the amino acid, in accordance with the following schedule:

| Amino Acid | Three-letter Symbol | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methione | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

In the present application, the L-form of any amino acid residue having an optical isomer is intended unless otherwise expressly indicated, e.g., by the symbol "[D-$X_n$]."

Compounds within the scope of the present invention can be obtained by modifying the disclosed formulae in numerous ways, while preserving the activity of the polypeptide compounds thus obtained. For example, while the amino acids of these compounds are normally in the natural L optical isomer form, one or more, usually two or less and preferably one amino acid may be replaced with the optical isomer D form, or a D,L-racemic mixture can be provided in the molecules comprising the polypeptide compound.

Additionally, a disulfide linkage may be present or absent in the compounds of the invention, as long as activity is maintained. As one skilled in the art would recognize, branched or cyclical chains may be produced by the formation of a peptide bond with amino acid side groups that contain amino or carboxyl moieties. Amino acids containing such side groups include, for example, glutamic acid (carboxyl group), aspartic acid (carboxyl group) and lysine (amide group). Branched or cyclical chains may also be produced through the formation of a covalent disulfide bond between amino acid residues having sulfur-containing side groups, such as cysteine.

As used herein, "protected" terminal amino group, refers to a terminal amino group coupled with any of various amino-terminal protecting groups traditionally employed in peptide synthesis. Examples of suitable groups include acyl protecting groups, for example, formyl, acetyl, benzoyl, trifluoroacetyl, succinyl, and methoxysuccinyl; aromatic urethane protecting groups, for example, benzyloxycarbonyl; and aliphatic urethane protecting groups, for example, tert-butoxycarbonyl or adamantyloxycarbonyl. Gross and Mienhofer, eds., *The Peptides*, vol. 3, pp. 3–88 (Academic Press, New York, 1981), disclose numerous suitable terminal amino protecting groups.

As used herein, "protected" terminal carboxyl group, refers to a terminal carboxyl group coupled with any of various carboxy-terminal protecting groups. As will be readily apparent to one skilled in the art, suitable groups include tert-butyl, benzyl or other acceptable groups linked to the terminal caroxyl group through an ester or ether bond.

Amino acid residues contained within the compounds, and particularly at the carboxy- or amino- terminus, can also be modified by methylation, amidation, acetylation or substitution with other chemical groups which can, for example, change the circulating half-life, resistance to proteases and solubility of the compounds without adversely effecting their activity.

In addition to the preceding definitions, the following abbreviations have been used throughout in describing the invention:

| | |
|---|---|
| BCA | bicinchoninic acid |
| BSA | bovine serum albumin |
| t-Boc | t-butyloxycarbonyl |
| Bzl | benzyl |
| °C. | degrees centigrade |
| DCM | dichloromethane |
| DIEA | diisopropyl ethyl amine |
| DMEM | Dulbecco's minimum essential medium |
| DMF | dimethyl formamide |
| HF | hydrogen fluoride |
| HOBT | 1-hydrooxybenzotriazole |
| HPLC | high performance liquid chromatography |
| mBHA | methylbenzhydrylamine |
| μg | microgram |
| μl | microliter |
| ml | milliliter |
| mM | millimolar |
| nm | nanometers |
| NMP | N-methylpyrrolidone |
| % | percent |
| PAM | phenylacetamidomethyl |
| PBS | phosphate buffered saline |
| TFA | trifluoroacetic acid |

B. Preferred Embodiments

The polypeptide compounds of the invention all contain the core pentapeptide sequence:

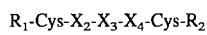

wherein:

$R_1$ is a protected or unprotected terminal amino group, including hydrogen, amino, acetyl or at least one amino acid residue or the desamino form thereof;

$X_2$, $X_3$, and $X_4$ are the same or different neutral/non-polar/ large/non-cyclic or neutral/polar/large/non-cyclic or neutral/ polar/small or basic/non-cyclic amino acid residues, preferably selected from the group consisting of valine, threonine, serine, and arginine;

$R_2$ is a protected or unprotected terminal carboxyl group including hydroxyl, carboxyl, or at least one amino acid residue, including carboxyamide or alkylamide forms thereof, preferably selected from the group consisting of lysine, glycine, and arginine;

the structure of the polypeptide is optionally cyclized through a bond between the cysteines, preferably a disulfide bond, or a bond between $R_1$ and $R_2$.

Particularly preferred are those embodiments wherein the sequence is selected from the group consisting of:

| | |
|---|---|
| CSVTCG | |
| CSVTCG—NH$_2$ | |
| CSVTCG | (disulfide linked) |
| CSTSCG | |
| CSTSCG—NH$_2$ | |
| CSTSCG | (disulfide linked) |
| CSTSCG—NH$_2$ | (blocked Cys residues) |
| CRVTCG | |
| CRVTCG | (disulfide linked) |
| CRVTCG—NH$_2$ | |
| RCRVTCG | (disulfide linked) |
| CSVTCK | |
| CSVTCR—NH$_2$ | |
| CSRTCG | |
| CRVTCG—NH$_2$ | (disulfide linked) |
| CRTSCG—NH$_2$ | |
| CSTSCR—NH$_2$ | |
| CRVTC—NH$_2$ | |
| CSTSC | |

Compounds within the scope of the present invention can be synthesized chemically by means well known in the art such as, e.g., solid phase peptide synthesis. The synthesis is commenced from the carboxy-terminal end of the peptide using an alpha-amino protected amino acid. t-Butylocarbonyl (Boc) protective groups can be used for all amino groups even though other protective groups are suitable. See Stewart et al., "Solid-Phase Peptide Synthesis," W. H. Freeman Co., San Francisco (1969) and Merrifield, *J. Am. Chem. Soc.* 85:2149–2154 (1963), Vale et al., *Science* 213, 1394–1397 (1981), and Marke et al., *J. Am. Chem. Sci.* 103, 3178 (1981). Other preparative methods which may be employed include the process of *Houghton Proc. Natl. ACAD Sci.* 82:5132 (1981), or another preferable synthesis procedure particularly for small branched or cyclic chain peptides which would include conventional liquid phase processes. The liquid phase process, as well as other synthesis methods are described in "Principle of Peptide Synthesis" M. Bodansky Ed. (Spring-Verlag 1984. These and other methods of peptide synthesis are also exemplified by U.S. Pat. Nos. 3,862,925, 3,842,067, 3,972,859, 4,105,602, 4,683,291, 4,244,946, and 4,305,872.

Conveniently, compounds may be synthesized using manual techniques or automatically employing, for example, an Applied BioSystems 430A Peptide Synthesizer (Foster City, Calif.) or a Biosearch SAM II automatic peptide synthesizer (Biosearch, Inc., San Rafael, California), following the instructions provided in the instruction manual supplied by the manufacturer.

Although a purity of greater than 95 percent for the synthesized peptide is preferred, lower purity may be acceptable. To obtain cyclic peptides, where for example the two cysteine amino acids are bonded or where the residues contain a disulfide bridge which may be formed by oxidizing of a dilute aqueous solution of the peptide with $K_3[Fe(CN)_6]$. Other means of cyclizing which are known in the art may also be utilized. The stabilized cyclized peptide of the present invention can also be prepared by forming a peptide bond between non-adjacent amino acid residue. A procedure for forming such peptide bond is provided in Schiller et al., *Int. J. Peptide Protein Res.* (1985) 25:171.

It will be readily appreciated by those having ordinary skill in the art of peptide synthesis that the intermediates which are constructed in accordance with the present disclosure during the course of synthesizing the present compounds are themselves useful compounds and are thus within the scope of the invention.

Alternatively, selected compounds of the present invention can be produced by expression of recombinant DNA constructs prepared in accordance with well-known methods. Such production can be desirable to provide large quantities or alternative embodiments of such compounds.

C. Administration

Compounds of the present invention have thrombospondin-like activity in the intact animal. Compounds of the present invention and compositions containing them which are shown to have the physiological effect of inhibiting or mimicing the effect of intact thrombospondin find use in numerous therapeutic and prophylactic applications, such as cancer therapy, wound healing, thrombotic or thrombolytic conditions, angiogenesis, or cell attachment.

Thus the present invention also provides compositions containing an effective amount of compounds of the present invention, including the nontoxic addition salts, amides and esters thereof, which may, alone, serve to provide the above-recited therapeutic benefits. Such compositions can also be provided together with physiologically tolerable liquid, gel or solid diluents, adjuvants and excipients.

These compounds and compositions can be administered to animals for veterinary use, such as with domestic animals, and clinical use in humans in a manner similar to other therapeutic agents. In general, the dosage required for therapeutic efficacy will range from about 1 µg to 300 mg/kg, more usually 10 µg to 30 mg/kg of the host body weight. Alternatively, dosages within these ranges can be administered by constant infusion over an extended period of time, usually exceeding 24 hours, until the desired therapeutic benefits have been obtained.

Typically, such compositions are prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiologically tolerable and compatible with the active ingredient. Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH buffering agents, and the like.

The compositions are conventionally administered parenterally, by injection, for example, either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides: such suppositories may be formed from mixtures containing the active ingredient in the range of 0.5% to 10%, preferably 1%–2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and contain 10%–95% of active ingredient, preferably 25%–70%. These oral formulations include formulations designed to protect the peptide until it can be absorbed.

The peptide compounds may be formulated into the compositions as neutral or salt forms. Pharmaceutically acceptable non-toxic salts include the acid addition salts (formed with the free amino groups) and which are formed with inorganic acids such as, for example, hydrochloric or phosphoric acids, or such organic acids as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In addition to the compounds of the present invention which display thrombospondin-like activity, compounds of the present invention can also be employed as intermediates in the synthesis of such useful compounds.

The compounds of the invention can be homopolymerized to themselves (i.e., (peptide)n) or, heteropolymerized to one another (i.e., (peptide 1-peptide 2). The compounds can also be cyclized through disulfide or other means. The compounds can also be conjugated to biocompatible polymeric compounds, such as BIOPOL™ (W. R. Grace & Co.-Conn.).

While not wishing to be bound by any theory, it is believed that the compositions of the invention act as agonists or antagonists to native thrombospondin. These compounds are also believed to act as agonists or antagonists to circumsporozoite protein, thrombospondin related anonymous protein, antistasin, and properdin complement protein. Further, since the compounds of the invention are small in size (relative to intact thrombospondin) the properties which they exhibit are more likely to be specific in nature, as opposed to the actions of other generally adhesive compounds such as RGD containing compounds (the sequence of which is found in over a hundred proteins) and fibronectin. The side effects of the peptide compounds of the invention are greatly reduced when compared with these broadly adhesive compounds.

D. Use

As stated previously, the compounds of the invention can be used in a variety of biological, prophylactic or therapeutic areas. It is contemplated that these compounds are useful in prevention or treatment of any disease state or conditions wherein thrombospondin-like activity plays a role. These disease states and conditions include, but are not limited to, metastasis, wound healing, thrombotic conditions, angiogenesis, and cell proliferation. Antibodies directed against the compounds of the invention are also useful as diagnostic reagents, therapeutics, or carriers of other compounds. The compounds can also be used in biomedical devices.

Numerous in vitro and in vivo assays can be used to demonstrate compounds having thrombospondin-like activity. These assays include, but are not limited to, cell adhesion assays, platelet aggregation assays and cell proliferation assays.

METASTASIS

Metastasis is the spread of disease from one part of the body to another unrelated to it, as in the transfer of the cells of a malignant tumor by way of the bloodstream or lymphatics. It is believed that metastasis is effected through a cascade mechanism which includes adhesion of tumor cells to endothelium, retraction of the endothelium, matrix degradation of the basement membrane and invasion of the tumor cells into the bloodstream. Intervention at any phase in this cascade could be beneficial to the treatment or prevention of metastatic cancers.

The native thrombospondin molecule has been shown to potentiate tumor cell metastasis (Tuszynski et al., *Cancer Research* (1987) 47:4130–4133). The mechanisms by which the thrombospondin potentiation occurs are not presently well understood.

Antimetastasis activity is characterized by the ability of the compounds to bind to melanoma cells in vitro (Tuszynski et al., *Anal. Bio.* (1990) 184:189–91), and the ability to reduce the size and number of tumor colonies in vivo (Tuszynski et al. *Cancer Research* (1987) 47:4130–4133).

The compounds of this invention are useful as antimetastatic agents, particularly useful as anti-pulmonary metastatic agents. These compounds inhibit the adhesion of metastatic tumor cells, particularly those which are responsive to thrombospondin. The compounds also reduce tumor colony number as well as tumor colony size.

There are a number of mechanisms by which such antimetastatic activity can be occurring. The peptides can be cytotoxic, or inhibit cell proliferation. As inhibitors of cell proliferation, the compounds can act to (1) inhibit mitogenesis, (2) inhibit angiogenesis, or (3) activate the complement pathway and the associated killer cells.

The compounds of the invention can also find use in biomedical devices. Since the compounds have the ability to promote the attachment of metastatic tumor cells, it is possible to coat a biomedical device with the compounds to effect the removal of circulating tumor cells from blood or lymph. The biomedical device is also useful to trap hepatomas.

Another use of the compounds is as a carrier to target toxins, drugs, hormones or imaging agents to metastatic tumor cells for diagnostic or therapeutic purposes. These carriers would also bind to hepatomas.

WOUND HEALING

Wound healing is the closure of wounds and can be divided into four essential components: inflammation, angiogenesis, collagen deposition and epithelialization. All four components play a role in the healing of wounds.

Wound healing activity is characterized by the ability of the compounds to show angiogenic activity, the ability of the compounds to stimulate collagen deposition and DNA synthesis in the in vivo sponge model or the ability of the compounds to improve wound healing or reduce healing time in an in vivo partial or full thickness wound model.

ANTI-PLATELET AGGREGATION

Platelet aggregation is a normal and beneficial process to stop bleeding of damaged tissue. However, platelet aggregation can cause problems following cardiovascular treatment such as angioplasty, thrombolytic therapy or vascular grafting. Platelets contain as much as 25% of the TSP protein in the total alpha granular platelet secreted-protein. Therefore, introduction of a peptide containing the pentapeptide sequence which is conserved in the TSP molecule and which binds to receptors on the surface of a platelet can prevent the platelet from aggregating and forming a clot.

A drug based on the pentapeptide is expected to be an adjunct to angioplasty and thrombolytic therapy for use with other clot-dissolving agents which are currently in the market (e.g., tPA, streptokinan). Such an agent does not aggravate bleeding or have the risk of side effects common to synthetic anti-platelet drugs. Additionally, such a peptide can help to keep open small diameter vascular grafts (such as those used in heart by-pass surgery). Similar applications are envisioned for patients at risk for stroke.

Anti-platelet aggregation activity is characterized by a number of assays, including (1) inhibition of ADP or thrombin-induced platelet aggregation in washed platelets; (2) inhibition of ADP-induced platelet aggregation in platelet-rich plasma; and (3) inhibition of collagen induced platelet aggregation measured in vivo.

ANGIOGENESIS

Angiogenesis is the formation of blood and lymph vessels. Angiogenesis is essential during development, in wound healing and for the growth of solid tumor. Angiogenesis is a complex process, requiring the sprouting and migration of endothelial cells, their proliferation and their differentiation into a tube like structure and the production of a basement membrane matrix around the vessel (Herbert et al. 1988, *L. Cell, Biol.* 106, 1365–1373). Angiogenesis is also essential to tumor development and growth. Prevention of angiogenesis can inhibit solid tumor growth. Use of the compounds of this invention can inhibit one or more steps in the cascade process of angiogenesis and therefore such peptide may be useful clinically to inhibit metastasis. The compounds of this invention are useful in the modulation of angiogenesis, particularly in enhancing wound healing, inhibiting or preventing tumor growth. Standard angiogenesis assays are well known in the art.

ADHESION AND CELL ATTACHMENT

The peptides of the present invention can be used for preparing a surface for optimal cell culture, and for prosthetic materials to promote bonding with surrounding tissue. These peptides can be useful as a cell attachment protein to provide a substrate to which cells will attach by treating a hydrophobic surface such as untreated synthetic plastic resin and especially materials which are used for different membrane applications, e.g., nitrocellulose or polysulfone or comparable material with the peptide. The cell attachment properties of the peptides can also be used to couple polypeptides covalently to a solid support such as gels or synthetic resins or long chain polysaccharide. This latter approach can be used for different affinity chromatography applications. Another important application of using such peptides are the use of the peptide in commercial cell attachment surfaces, wherein the particles are coated with gelatin, making it possible to grow the same adherent cells in a much smaller volume of media than would be possible in dishes. Medical devices can be designed for use with such peptides to attach cells to the surface in vivo, or even to promote the growth of a desired cell type on particular surfaces prior to grafting. An example of this is attachment of islet cells to a membrane or growth of endothelial cells on a prosthetic blood vessel or vascular graft. Such peptides can find uses in coating a patch graft or the like for aiding in wound healing.

ANTIBODIES

Antibodies, both monoclonal and polyclonal, directed to peptide compounds of the present invention are useful in isolation and identification of the subject protein from where the peptides are derived, and the present invention also pertains to such antibodies. To prepare antibodies, any one of a number of techniques which are known in the art can be employed. In one such technique, polyclonal antibodies may be synthesized by injecting an animal (for example, a rabbit) with one or more compounds of the invention. After injection, the animal naturally produces antibodies to these compounds. When the antibody level rises to a sufficient level, antibody-containing blood, called antiserum, is then drawn from the animal, and the compound-specific antibody is isolated from other antibodies in the antiserum by any one of a number of separation techniques (for example, affinity chomatography). Monoclonal antibodies may be prepared using the technique of Kohler and Milstein, Nature 256, pp. 495–497 (1975).

Compounds of the present invention can also be used for preparing antisera for use in immunoassays employing labelled reagents, usually antibodies. Conveniently, the polypeptides can be conjugated to an antigen by means of dialdehydes, particularly from 4 to 6 carbon atoms and aliphatic, or carbodimide. These compounds and immunologic reagents may be labelled with a variety of labels such as chromophores, fluorophores such as, e.g., fluorescein or rhodamine, radioisotopes such as $^{125}$I, $^{35}$S, $^{14}$C, or $^{3}$H, or magnetized particles, by means well known in the art.

These labelled compounds and reagents, or labelled reagents capable of recognizing and specifically binding to them, can find use as, e.g., diagnostic reagents. Samples derived from biological specimens can be assayed for the presence or amount of substances having a common antigenic determinant with compounds of the present invention.

Thrombospondin levels are elevated in the serum of patients with metastatic breast and colon cancer (Tuszynski et al., *Thrombosis Haemostas* (1989) 62:418 and Smith et al., *Proceedings American Association of Clinical Oncology* (1990) 9:6). Antibodies against the peptides of the invention can be useful as reagents in diagnostic/prognostic assays for various types of cancer, including but not limited to, gastrointestinal tract (gastric, colonic, and rectal) carcinomas, breast carcinomas and hepatic carcinomas.

The polyclonal and monoclonal antibodies can find therapeutic use in a number of cancer therapies. First, the antibodies can be used to sequester thrombospondin. This is useful since thrombospondin mediates tumor cell metastasis. Second, the antibodies can be used to block thrombospondin present on the tumor cell surface. Third, cytotoxic drugs, hormones, or imaging agents can be coupled to the antibodies for use in cancer therapy. Fourth, a biomedical device can be coated with the antibodies to remove excess thrombospondin from serum or to remove cells which bear thrombospondin on the cell surface.

The peptides of the invention can also be used to isolate thrombospondin cell surface receptors from extracts of cells or cell membranes. Standard procedures such as affinity chromatography can be employed. The thrombospondin cell surface receptors can be used to develop better thrombospondin analogs or to remove excess thrombospondin from serum.

The following examples are provided by way of illustration, rather than implying any limitation of the subject matter.

EXAMPLES

The peptides of this invention can be synthesized by conventional methods of peptide synthesis. The preferred conventional methods use the procedures described in *Int. J. Pept. Proc. Res.* 21, 57–63 (1983). Also preferred is the solid phase synthesis of Merrified, *J. Amer. Chem. Soc.* 85, 2149–2154 (1963); *Science* 150, 178–185 (1965); *Ibid.* 232, 341–347 (1986). Solid phase synthesis is generally initiated from the C-terminal of the peptide by coupling a protected alpha amino acid to a suitable resin, e.g., phenylacetamidomethyl (PAM) polystyrene resin, or p-methylbenzhydrylamine (mBHA) resin when synthesizing a peptide with a C-terminal carboxyamide. During synthesis, suitable amino acid side-chain protecting groups are used as needed. Thus, aspartic acid is protected on the beta-carboxyl group as the benzyl ester and arginine is protected on the guanidino group by tosyl. After the desired peptide has been synthesized, the peptide is cleaved from the resin and protecting groups are removed by treatment with a reagent such as hydrogen fluoride (HF). The peptide can then be purified by high performance liquid chromatography (HPLC) or other such methods of peptide purification. Background information on the established procedures for solid phase peptide synthesis can be found in "Solid Phase Peptide Synthesis" by Stewart and Young, W. H. Freeman & Co., San Francisco, 1969.

In accordance with the above description, the following procedures were used for the chemical synthesis of novel synthetic peptides:

EXAMPLE 1

Synthesis of the Peptide Sequence CSVTCG with C Terminal Amide

An appropriate resin 4-methylbenzhydrylamine (MBHA) for C-terminal amide was sealed into polypropylene mesh packets (64μ). All packets were placed into a common vessel with $CH_2Cl_2$ and vigorously shaken to wash and swell the resin. All subsequent steps involved vigorous shaking to ensure adequate solvent transfer. The N-α-butoxycarbonyl was then removed by acidolysis using 55% trifluoroacetic acid (TFA)/$CH_2Cl_2$ for 30 minutes leaving the α-amino acid group in the TFA salt form. The packets were then washed with $CH_2Cl_2$ (2x), IPA (2x), and $CH_2Cl_2$ (2x) to remove excess TFA and prepare for neutralization. The IFA salt was neutralized by washing the packets three times with 5% diisopropylethylamine in $CH_2Cl_2$ for 2 minutes each. This was followed by two washes with $CH_2Cl_2$ to remove excess base. Packets were then removed from the common vessel and added to their respective 0.2M amino acid solutions which were prepared from computer generated information prior to neutralization. An equal volume of 0.2M dipropylcarbodiimide was then added to activate the coupling reaction. After coupling at room temperature for 1 hour, the packets were washed with dimethyl-formamide and $CH_2Cl_2$ and returned to the common vessel. This process was repeated for each amino acid. Cleavage occurred by reacting the peptide with 92.5% hydrogen fluoride/7.5% anisole at −10° C. to 0° C. over 90 minutes. Anisole was used as a scavenger to react with carbocations produced as a result of the side chain protecting group removal. This solution was then removed using a strong flow of $N_2$ followed by the use of aspirator vacuum, while maintaining the temperature at 0° C. Residual anisole was removed with 2 ethyl ether washes. The peptide was then extracted using 10% acetic acid.

The purity of the crude peptide was checked by analytical RP-HPLC using a Beckman System Gold with a Vydac C-18 column at a flow rate of 1 ml/min. The solvent system used was 0.05% aqueous TFA(A) and 0.05% TFA in acetonitrile (B) with a gradient of 5–65% B in 30 minutes measuring the absorbance at 215 μm). Purification was performed on Waters delta prep. 3,000 preparative HPLC with a Waters prep. Pak Nodule Radial Compression C18 column (25 cm×5 cm, 10–20μ). The solvent system was 0.05% aqueous TFA (A) and 0.05% TFA in acetontrile (B). Various linear gradients were used measuring the absorbance at 230 nm and collecting 40 ml fraction. The fractions were then analyzed on the Beckman analytical system. The desired fractions were pooled and lyophilized. The final dry product was analyzed one more time using analytical RP-HPLC. Typical HPLC chromatograms for this peptide after purification are shown in FIG. 1.

EXAMPLE 2

Chemical Synthesis of the Peptide Sequence CSVTCG Acid

An appropriate resin phenylacetamidomethyl (PAM) for C-terminal acid was sealed into polypropylene mesh packets (64μ). All packets were placed into a common vessel with $CH_2Cl_2$ and vigorously shaken to wash and swell the resin. All subsequent steps involved vigorous shaking to ensure adequate solvent transfer. The N-α-butoxycarbonyl is then removed by acidolysis using 55% trifluoroacetic acid (TFA)/$CH_2Cl_2$ for 30 minutes leaving the α-amino acid group in the TFA salt form. The packets were then washed with $CH_2Cl_2$ (2x), IPA (2x), and $CH_2Cl_2$ (2x) to remove excess TFA and prepare for neutralization. The TFA salt was neutralized by washing the packets three times with 5% diisopropylethylamine in $CH_2Cl_2$ for 2 minutes each. This was followed by two washes with $CH_2Cl_2$ to remove excess base. Packets were then removed from the common vessel and added to their respective 0.2M amino acid solutions which were prepared from computer generated information prior to neutralization. An equal volume of 0.2M diisopropylcarbodiimide was then added to activate the coupling reaction. After coupling at room temperature for 1 hour, the packets were washed with dimethylformamide and $CH_2Cl_2$ and returned to the common vessel. This process was repeated for each amino acid. Cleavage occurred by reacting the peptide with 91.5% hydrogen fluoride/7.5% anisole at −10° C. to 0° C. over 90 minutes. Anisole was used as a scavenger to react with carbocations produced as a result of the side chain protecting group removal. This solution was then removed using a strong flow of $N_2$ followed by the use of an aspirator vacuum, while maintaining the temperature at 0° C. Residual anisole is removed with two ethyl ether washes. The peptide is then extracted using 10% acetic acid.

Figure 2:
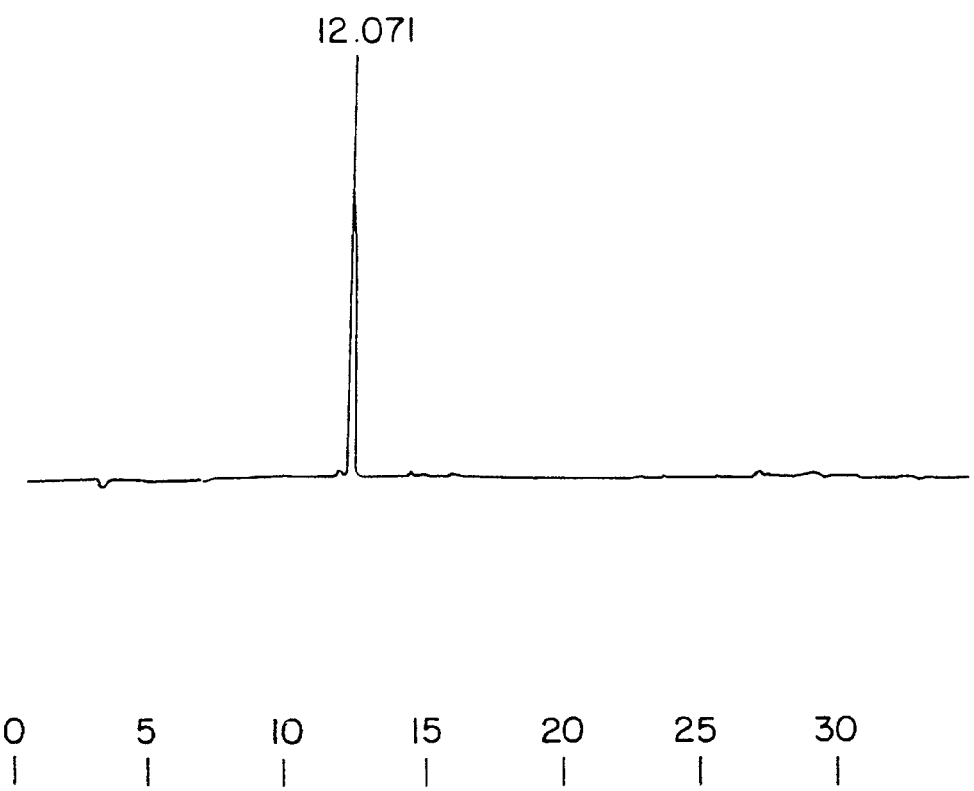
FIG. 2 shows the results of HPLC analysis on peptide CSVTCG.

The purity of the crude peptide was checked by analytical RP-HPLC using a Beckman System Gold with a Vydac C-18 column at a flow rate of 1 ml/min. The solvent system used was 0.05% aqueous TFA(A) and 0.05% TFA in acetonitrile (B) with a gradient of 5–65% B in 30 minutes measuring the absorbance at 215 nm. Purification was performed on Waters delta prep. 3,000 preparative HPLC with a Waters prep. Pak Nodule Radial Compression C18 column (25 cm×5 cm, 10–20μ). The solvent system was 0.05% aqueous TFA (A) and 0.05% TFA in acetonitrile (B). Various linear gradients were used measuring the absorbance of 230 nm and collecting 40 ml fraction. The fractions were then analyzed on the Beckman analytical system. The desired fractions were pooled and lyophilized. The final dry product was analyzed one more time using analytical RP-HPLC. Typical HPLC chromatogram for this peptide after purification are shown in FIG. 2.

EXAMPLE 3

Synthesis of cyclic CSVTCG-Acid

Cyclization of CSVTCG peptide was accomplished by dissolving the crude peptide of Example 2 (52 mg) in 500 ml deoxygenated water and the pH was adjusted to 8.5 with 28% $NH_4OH$ (solution A). $K_3Fe(CN)_6$ (1.75 g) was dissolved in 100 ml deoxygenated water and the pH was adjusted to 8.5 with 28% $NH_4OH$. This solution is called solution B.

Solution A was dropped into solution B in 2 hours and the mixture was allowed to stir 1 more hour. The pH was then adjusted to 4 with 10% AcOH and the solution was injected onto a prep.-HPLC. After purification a 28 mg peptide of 95% purity has been recovered.

Figure 3:
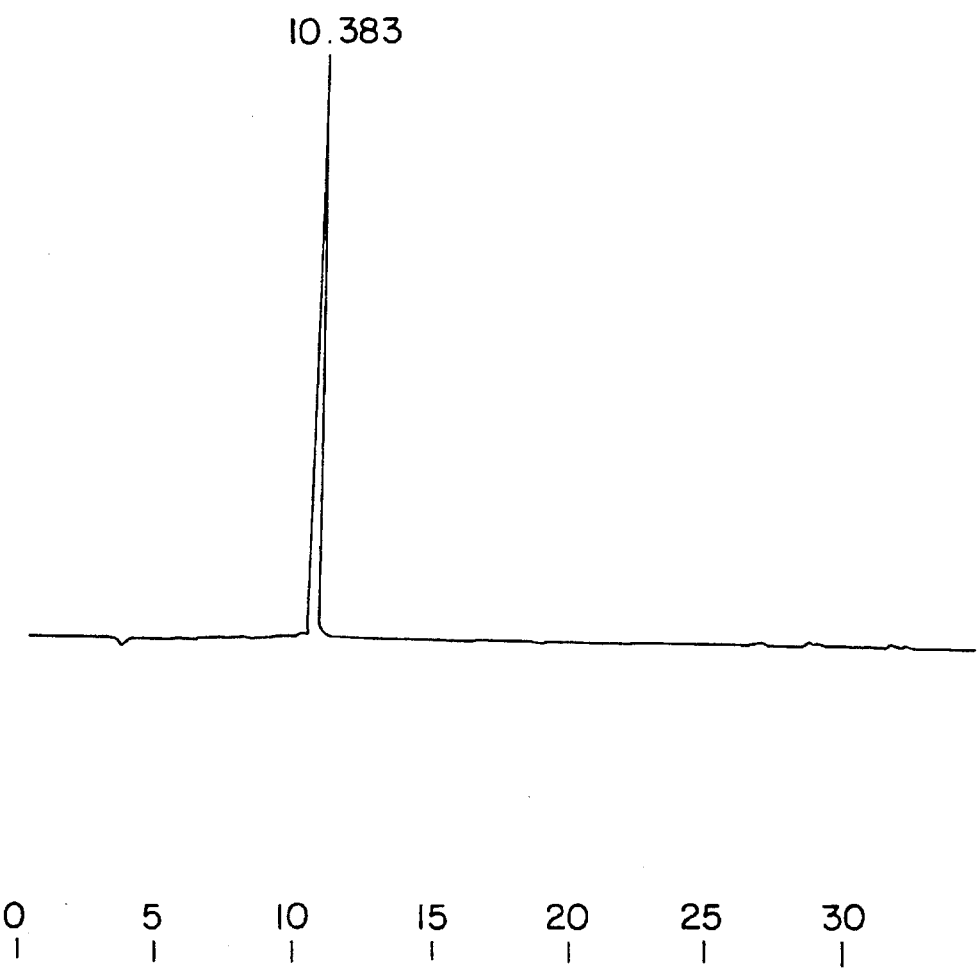
FIG. 3 shows the results of HPLC analysis on peptide CSVTCG which is cyclized via a disulfide bond.

The composition of the cyclic material was confirmed by analytical reverse phase HPLC and by Feb-MS. Typical HPLC chromatography is presented in FIG. 3.

EXAMPLE 4

Chemical Synthesis of Additional Peptides

Following the procedures outlined in Examples 1–3 and in *Int. J. Pept. Proc. Res.* 21, 57–65 (1983) with appropriate modification, the following peptides were synthesized. All peptides of the invention were tested for endotoxins using standard LAL assay procedures and found to be endotoxin free.

| | |
|---|---|
| CSTSCG | |
| CSTSCG—$NH_2$ | |
| CSTSCG | (disulfide linked) |
| CSTSCG—$NH_2$ | (blocked Cys residues) |
| CRVTCG | |
| CRVTCG | (disulfide linked) |
| CRVTCG—$NH_2$ | |
| RCRVTCG | (disulfide linked) |
| CSVTCK | |
| CSVTCR—$NH_2$ | |
| CSRTCG | |
| CRVTCG—$NH_2$ | (disulfide linked) |
| CRTSCG—$NH_2$ | |
| CSTSCR—$NH_2$ | |
| CRVTC—$NH_2$ | |
| CSTSC | |

EXAMPLE 5

Adhesion of $B_{16}F_{10}$ Melanoma Cells to TSP and Peptides

In this example a series of peptides were tested to determine the abilities of the peptides to bind $B_{16}F_{10}$ melanoma cells as compared to thrombospondin and fibronectin. It is believed that thrombospondin acts in metastasis through its adhesive properties. An assay was developed, generally in accordance with the disclosure of Tuszynski et al. (*Anal. Bio.* (1990) 184:189–91) which evaluates the ability of melanoma cells to adhere to the thrombospondin fragments or analogs of the invention. In this assay, thrombospondin (purified by the method of Tuszynski et al., *J. Biol. Chem.* (1985) 260:12240–5) and fibronectin (Sigma Chemical Co., Missouri) served as positive controls, bovine serum albumin (BSA) (Sigma Chemical Co.) served as the negative control. Thrombospondin analogs of the invention were synthesized as described in Examples 1–4. Two micrograms of peptide or control proteins were air dried overnight on the wells of a 96-well microtiter plate. Wells were then washed with HEPES-buffered saline and blocked for 1 hour with 1% fatty acid free BSA in HEPES-buffered saline.

The mouse $B_{16}F_{10}$ melanoma cells were grown and harvested during log phase of growth using standard procedures. The harvested cells were washed two times in serum-free Dulbecco's minimum essential medium (DMEM) (Flow Laboratories) and suspended in HEPES-buffered saline, containing 5 mM glucose and 100 µM $MgCl_2$ at a final concentration of $4\times10^5$ cells/ml. Of the cell suspension 200,000 cells per well was added to each well of the microtiter dish containing the various ligands and the dish incubated at 37° C. in a $CO_2$ incubator for 30 minutes. Nonadherent cells were removed by aspiration and the wells washed three times with 200 µl of PBS. The total cell-associated protein was determined by dissolving the attached cells directly in the microtiter wells with 200 µl of the Pierce BCA working solution (*Pierce Chem. Co. Booklet No.* 23225 (1987)). The plate was covered with an adhesive mylar sheet (Flow Labs) and incubated at 60° C. for 30 minutes. Plates were allowed to cool to room temperature, cover sheets were removed, and the absorbance of each well was determined at 562 nm with a microtiter plate reader (Biotek, Burlington, Vt.) Absorbances were converted to number of adherent cells by means of an empirically determined conversion factor.

Figure 4:
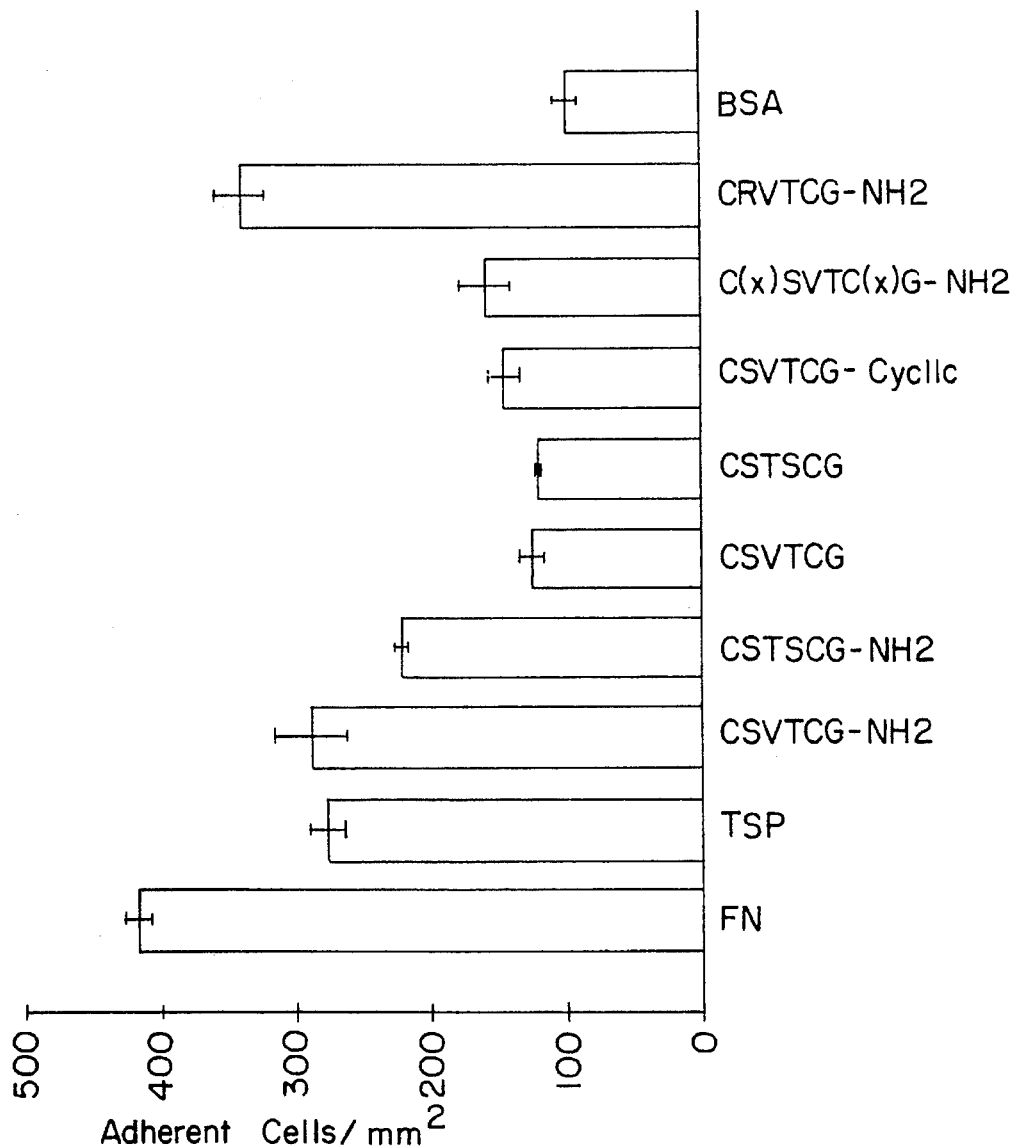
FIG. 4 shows the ability of the peptides of the invention to inhibit adhesion of melanoma cells.

The results shown in FIG. 4 indicate that the peptides of the invention display adhesive properties.

EXAMPLE 6

The Effect of Peptides on Collagen Dependent Adhesion of $B_{16}F_{10}$ Melanoma Cells.

Figure 5:
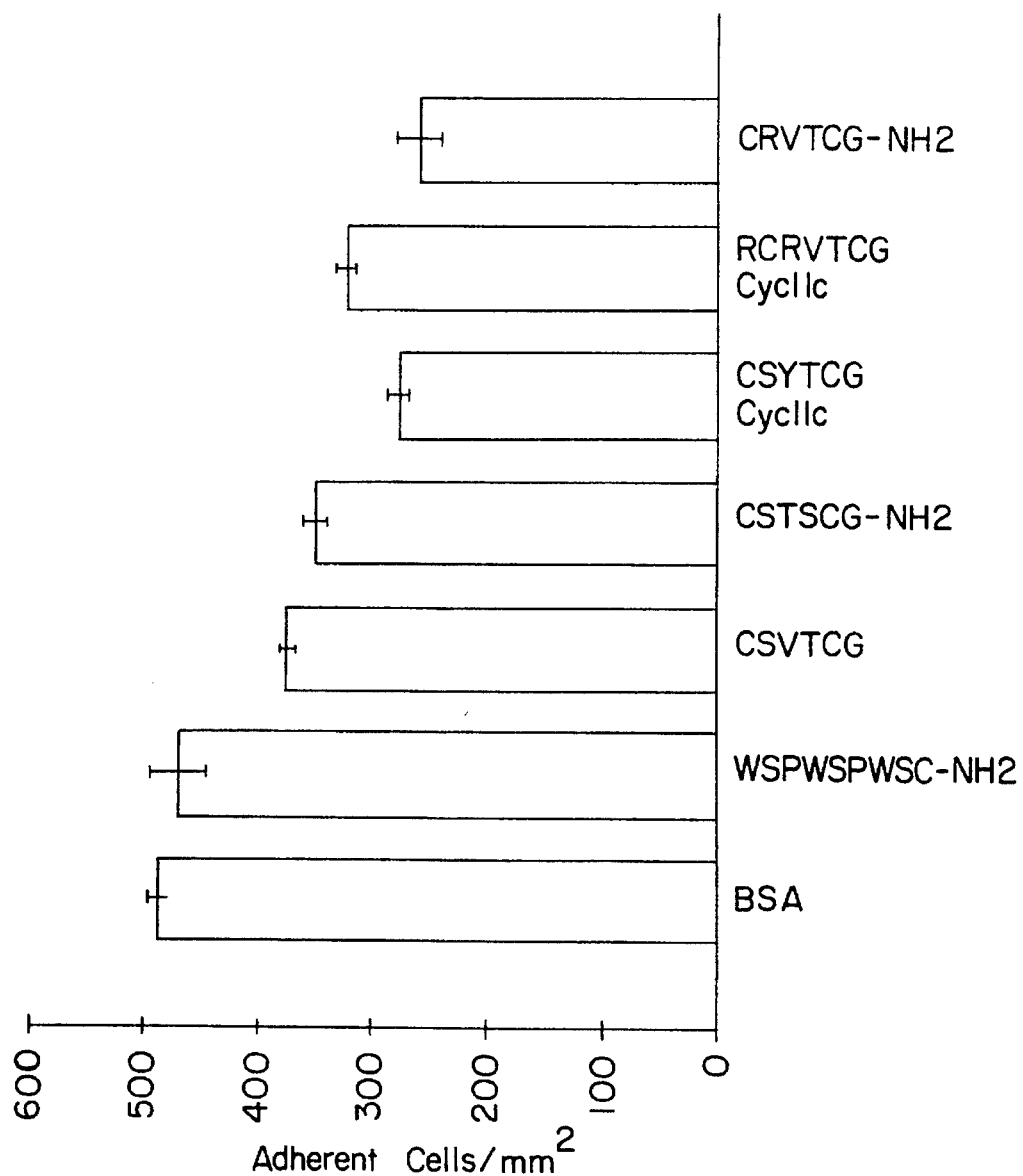
FIG. 5 shows the ability of the peptides of the invention to act in collagen dependent melanoma cell adhesion.

Two micrograms of collagen in 5 mM acetic acid were adsorbed to wells overnight at 4° C. Wells were then washed with HEPES-buffered saline and blocked for 1 hour with 1% fatty acid free bovine serum albumin (BSA) in HEPES buffered saline. A suspension of $B_{16}F_{10}$ cells in HEPES-buffered saline, containing 5 mM glucose (200,000 cells per well) and 100 µM $MnCl_2$ were preincubated for 15 minutes at 37° C. in either buffer or in buffer containing 100 µg/ml peptide or 100 µg/ml BSA. The cell suspensions were then added to collagen-coated wells and incubated for 30 minutes at room temperature. Non-adherent cells were removed by aspiration, and adherent cells determined by measurement of cell-associated protein as previously described in Example 5. The results shown in FIG. 5 indicate that the peptides of the invention inhibit the binding of the melanoma cell to collagen.

EXAMPLE 7

The Effect of Peptides on $B_{16}F_{10}$ Lung Tumor Cell Metastasis

The in vivo model used to demonstrate the antimetastatic activity of the peptide compounds of the invention is described by Tuszynski et al. (*Cancer Res.* (1987) 47:4130–4133). Briefly, C57 black mice were intravenously injected with $1\times10^5$ $B_{16}F_{10}$ mouse melanoma cells in the presence of either control buffer (Hepes buffered saline, pH 7.4), or 1 mg of the designated peptide compound of the invention. Five or six animals were used for each compound. Peptides tested in the assay had no effect on cell viability as measured by Trypan blue dye exclusion. In addition, the peptides at 1 mg/ml did not effect cell growth after 24 hours of co-culture. After 14 days, the mice were sacrificed and the number of lung tumors counted.

Figure 6:
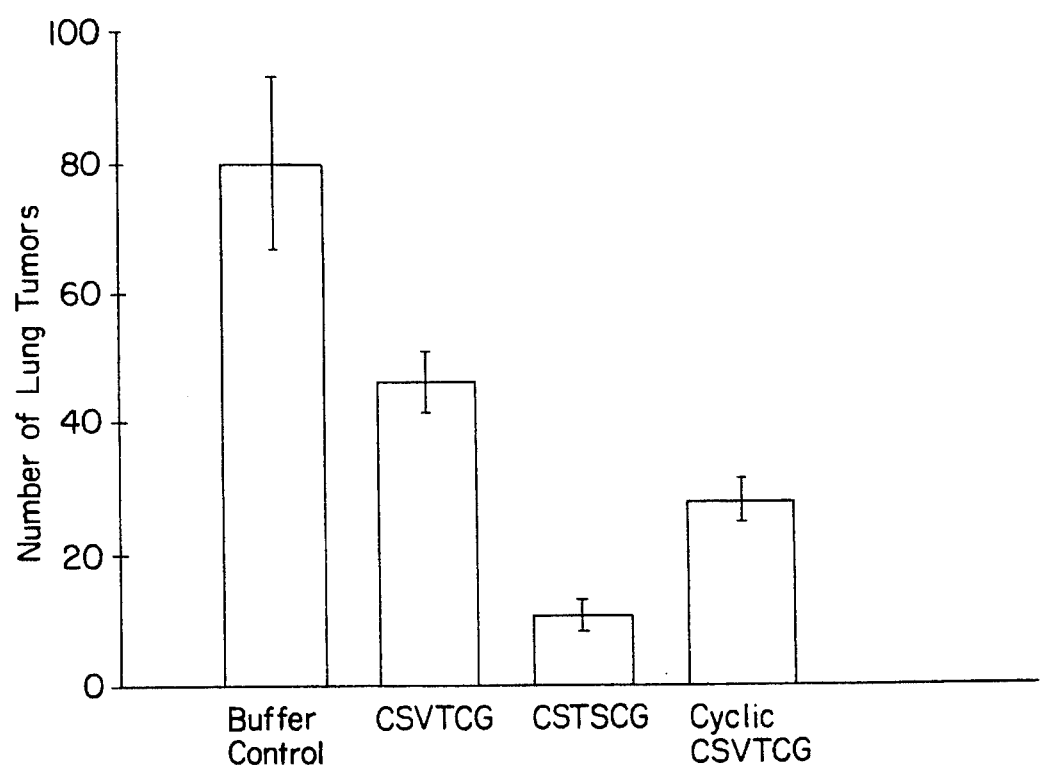
FIG. 6 demonstrates that in vivo the peptides of the invention have antimetastatic activity.
Figure 7:
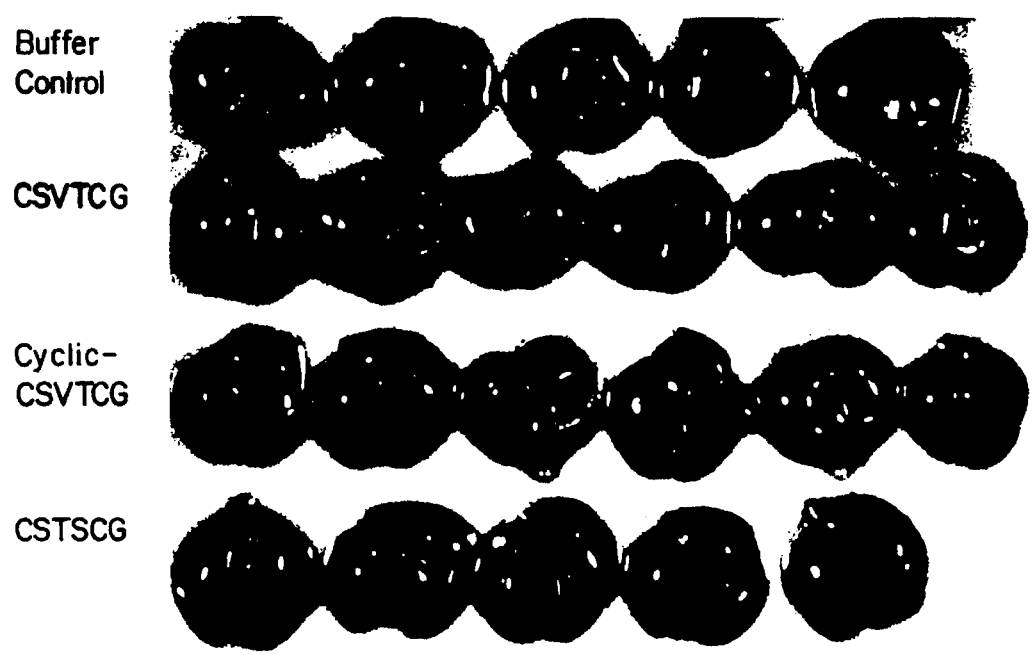
FIG. 7 compares the lungs of mice treated with and without the peptides of the invention in the presence of melanoma cells.

The results shown in FIG. 6 indicate the peptides of the invention have antimetastatic activity. The bar graphs show the mean number of lung tumors observed in the treatment groups and the error bars represent the standard error of the mean. FIG. 7 shows representative lungs from each of the treatment groups.

EXAMPLE 8

Platelet Aggregation Assay

Platelet aggregation was monitored on a single-channel aggregometer equipped to measure luminescence (Chromo-Log, Havertown, Pa.). Platelet-rich-plasma (PRP) was obtained from whole blood anti-coagulated with 0.38% sodium citrate by centrifugation at 150× g for 20 minutes.

Figure 8:
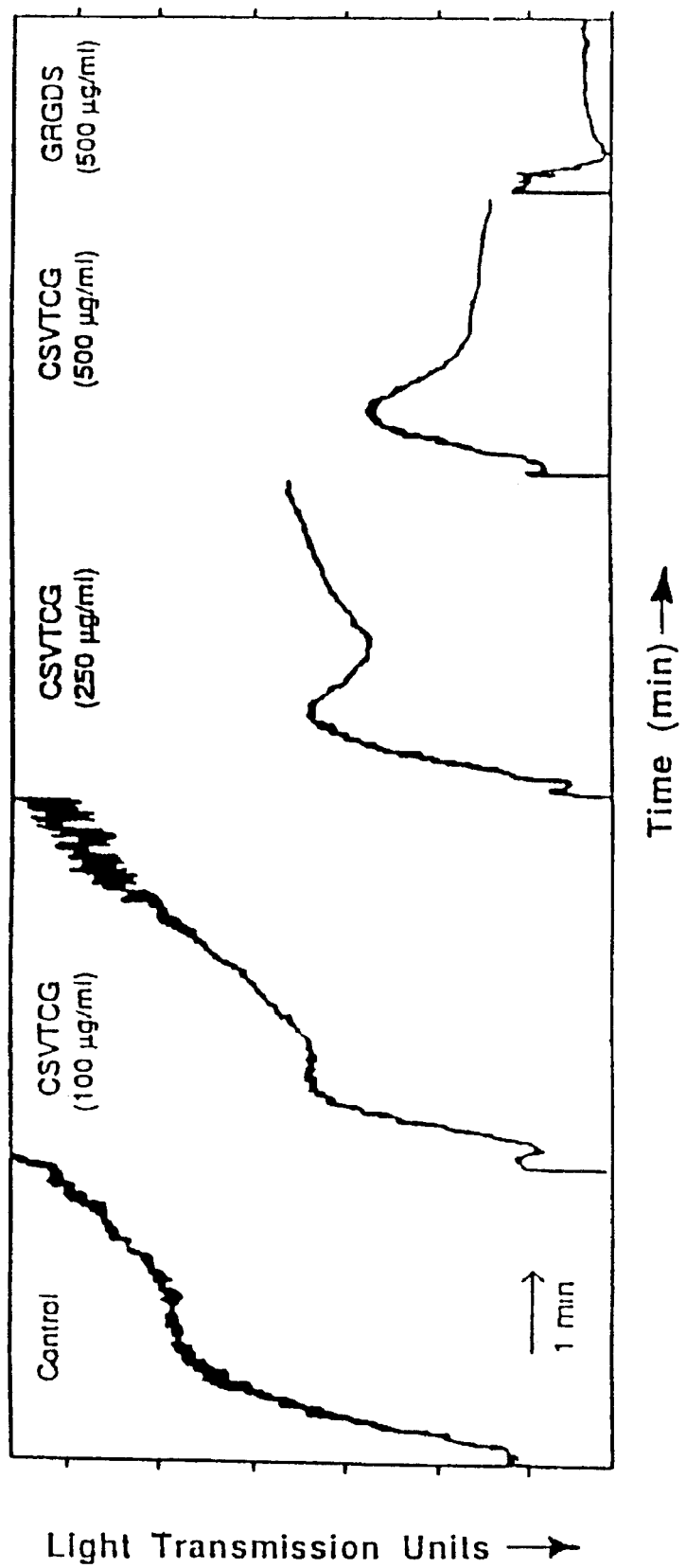
FIG. 8 shows the ability of the peptides of the invention to inhibit ADP-induced platelet aggregation.

The effect of peptides on ADP-induced platelet aggregation is shown in FIG. 8. 0.5 ml aliquots of platelet-rich-plasma were aggregated by stirring with 2 uM ADP in the presence of various concentrations of CSVTCG and GRGDS. Aggregation was measured at 37° as decrease in optical absorbance vs. time in a chrono-log aggregometer and is shown in FIG. 8. Peptides designated in each panel are represented by their amino acid sequence using the one letter code.

EXAMPLE 9

The Effect of Peptides on Collagen-Induced Platelet Aggregation.

Figure 9:
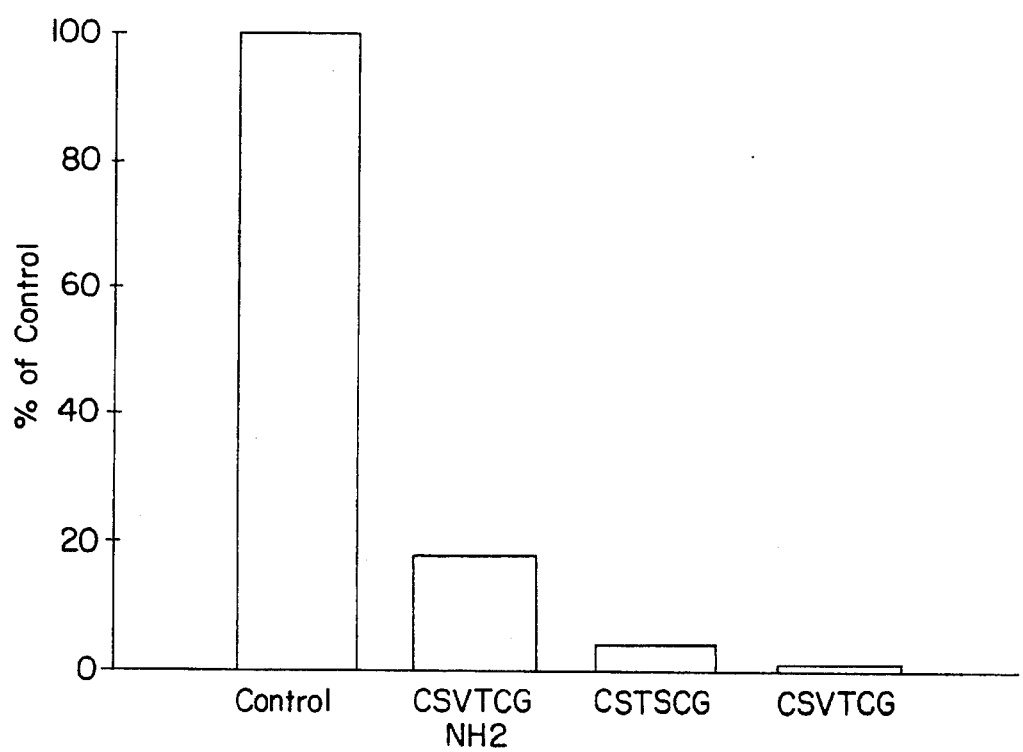
FIG. 9 shows the ability of the peptides of the invention to inhibit collagen-induced platelet aggregation.

Washed human platelets were suspended in HEPES-buffered saline, containing 5 mM glucose and 350 µg/ml BSA. 0.5 ml aliquots of platelets were aggregated by stirring with 5 µg/ml collagen in the presence of 500 µg/ml of various peptides. Aggregation was measured at 37° C. as decrease in optical absorbance vs. time in a Chrono-log aggregometer and is shown in FIG. 9. 100% aggregation was defined as the maximal decrease in absorbance measured in the absence of peptide. % of control was calculated as the decrease in absorbance measured in the presence of peptide divided by the decrease in absorbance measured in the absence of peptide times 100. Peptides are designated under each bar graph by their amino acid sequence represented using the one letter code.

EXAMPLE 10

Dose-Response of CSVTCG on Collagen-Induced Platelet Aggregation.

Figure 10:
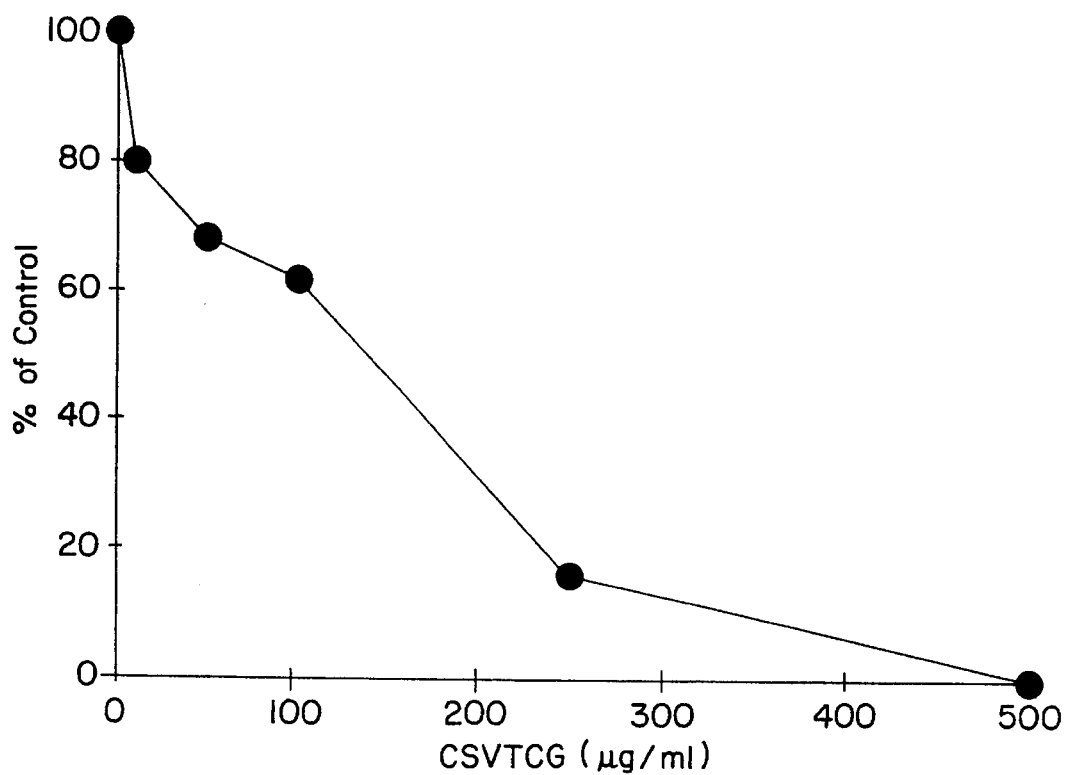
FIG. 10 shows a dose response of the ability of peptide CSVTCG to inhibit collagen-induced platelet aggregation.

Washed human platelets were suspended in HEPES-buffered saline, containing 5 mM glucose and 350 µg/ml BSA. 0.5 ml aliquots of platelets were aggregated by stirring with 5 µg/ml collagen in the presence of various concentrations of CSVTCG. Aggregation was measured at 37° C. as decrease in optical absorbance vs. time in a chrono-log aggregometer and is shown in FIG. 10. 100% aggregation was defined as the maximal decrease in absorbance measured in the absence of peptide. % of control was calculated as the decrease in absorbance measured in the presence of peptide divided by the decrease in absorbance measured in the absence of peptide times 100.

EXAMPLE 11

Adhesion of Human Platelets to TSP and Peptides.

Figure 11:
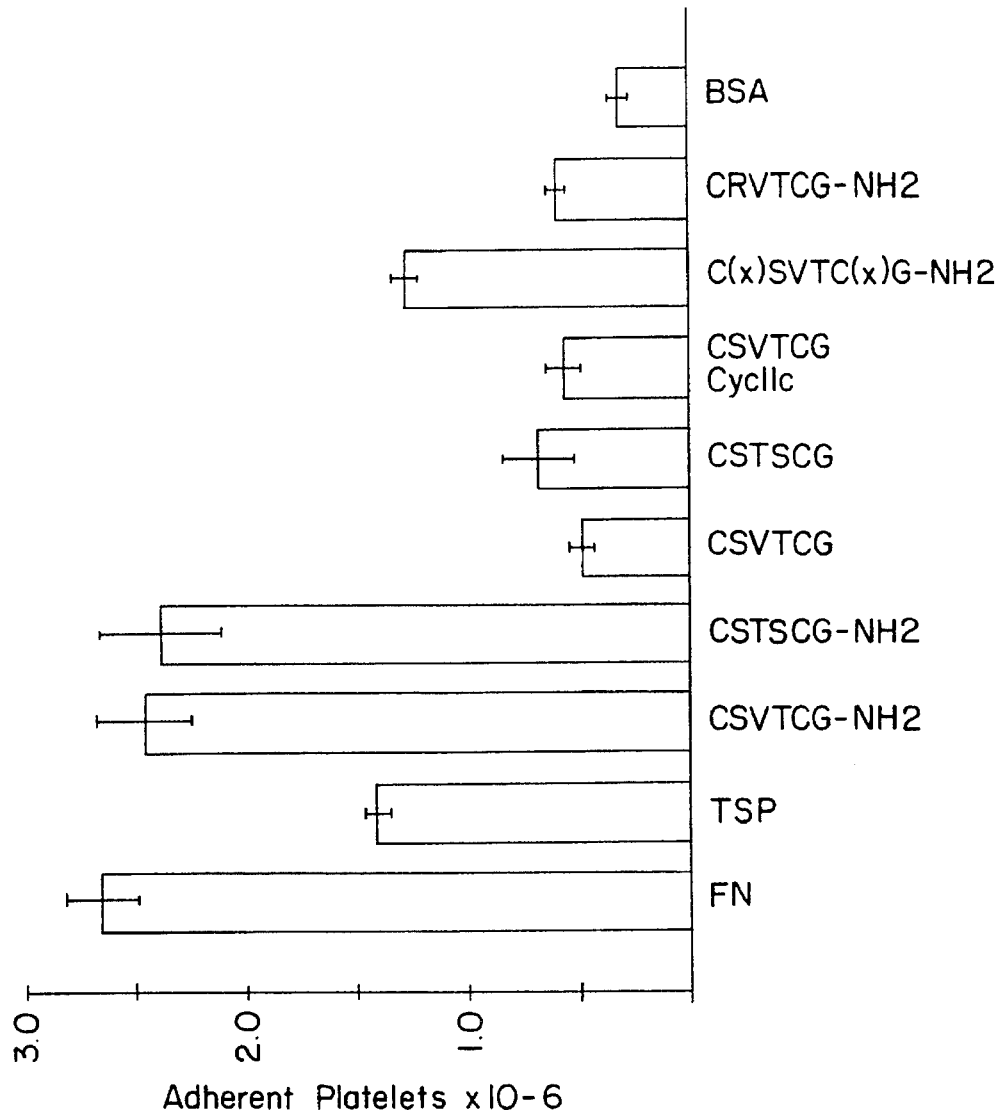
FIG. 11 shows the ability of the peptides of the invention to support the adhesion of human platelets.

The number of adherent platelets was essentially determined as previously described (Tuszynski et al., *Anal. Bio. supra*). Briefly, 100 µl of 5×10$^8$ platelets/ml washed as previously described (Tuszynski et al., (1988) *Blood* 72, 109–225) were added to microtiter plates, the wells of which were treated with 2 µg of peptide or protein solution (HEPES buffered saline, pH 7.4). Solutions were dried at room temperature after incubation in a fume hood overnight. Wells were then washed with HEPES-buffered saline and blocked for 1 hour with 1% fatty acid free bovine serum albumin (BSA) in HEPES buffered saline. Platelets (100 µl) were incubated in the wells for 30 minutes and non-adherent platelets were removed by aspiration. Wells were washed 3× with 200 µl of Hepes buffered saline, pH 7.4. The number of adherent platelets was determined by measuring the platelet-derived protein using the BCA protein assay. The results are shown in FIG. 11. The label under each bar designates the protein or peptide used to coat the well. Proteins used were thrombospondin (TSP), fibronectin (FN), and bovine serum albumin (BSA). Peptides are designated under each bar graph by their amino acid sequence represented using the one letter code. The peptide having blocked cys residues is given as C(x)SVTC(x)G-NH-2, where x represents the blocking group ACM. A suspension of platelets in Hepes-buffered saline, containing 5 mM glucose and 350 µg/ml BSA (5×10$^7$ platelets per well) were incubated in each well for 30 minutes, nonadherent platelets removed by aspiration, and adherent cells determined by measurement of cell-associated protein as previously described (Tuszynski et al., (1990) 184:189–191). The data is a representative of 2–3 experiments and data points in each experiment are the mean of three determinations, and the error bars represent the standard error of the mean (SEM).

EXAMPLE 12

Activity of Pentapeptides

The pentapeptides CRVTC-NH$_2$ and CSTSC will be synthesized and tested for activity in the assays described in Examples 5–11. The results of the assays are expected to support the present invention.

What is claimed is:

1. A method for inhibiting or enhancing angiogenesis activity comprising administering to a patient in need of such treatment at least one polypeptide selected from the group consisting of:

CSVTCG—NH$_2$
CSVTCG
CSTSCG
CSTSCG—NH$_2$
CRVTCG
CRVTCG—NH$_2$
RCRVTCG
CSVTCK
CSVTCR—NH$_2$
CSRTCG
CRVTCG—NH$_2$
CRTSCG—NH$_2$
CSTSCR—NH$_2$
CRVTC—NH$_2$
CSTSC and
CSTSCCSVTCG, wherein said polypeptide may be non-cyclic or is cyclized via the cysteine residues contained therein and wherein said polypeptide may optionally comprise an amino-terminal and/or carboxy-terminal protecting group.

2. The method of claim 1, wherein the polypeptide is cyclized by the formation of a disulfide bond between the cysteine residues contained therein.

3. The method of claim 1, wherein the terminal amino group of said polypeptide is protected by attachment of an amino-terminal protecting group.

4. The method of claim 3, wherein the amino-terminal protecting groups are selected from the group consisting of acyl protecting groups, aromatic urethane protecting groups and aliphatic urethane protecting groups.

5. The method of claim 4, wherein said acyl protecting groups are selected from the group consisting of formyl, acetyl, benzoyl, trifluouroacetyl, succinyl and methoxysuccinyl.

6. The method of claim 4, wherein the aromatic urethane protecting group is benzyloxycarbonyl.

7. The method of claim 4, wherein the aliphatic urethane protecting group is tert-butoxycarbonyl or adamantyloxycarbonyl.

8. The method of claim 1, wherein the terminal carboxyl group of said polypeptide is protected by attachment of a carboxy-terminal protecting group.

9. The method of claim 8, wherein the carboxy-terminal protecting group is tert-butyl or benzyl.

10. The method of claim 1 wherein the cysteine residues contained in said polypeptide are protected.

* * * * *